United States Patent [19]

Rumpel

[11] Patent Number: 5,276,494
[45] Date of Patent: Jan. 4, 1994

[54] HIGH-SPEED PRINTING DEVICE HAVING A PARTICLE TRAP ARRANGED IN THE PAPER CHANNEL

[75] Inventor: Peter Rumpel, Feldkirchen, Fed. Rep. of Germany

[73] Assignee: Siemens Nixdorf Informationssystem AG, Fed. Rep. of Germany

[21] Appl. No.: 768,187

[22] PCT Filed: Dec. 1, 1989

[86] PCT No.: PCT/DE89/00747
§ 371 Date: Oct. 7, 1991
§ 102(e) Date: Oct. 7, 1991

[87] PCT Pub. No.: WO90/12344
PCT Pub. Date: Oct. 18, 1990

[30] Foreign Application Priority Data

Apr. 5, 1989 [DE] Fed. Rep. of Germany ....... 3911026

[51] Int. Cl.$^5$ .......................................... G03G 21/00
[52] U.S. Cl. .................... 355/309; 271/258; 355/316
[58] Field of Search ............. 355/308, 309, 316, 318; 271/3, 3.1, 256, 258; 15/256.51, 256.52

[56] References Cited

U.S. PATENT DOCUMENTS

| | | | |
|---|---|---|---|
| 3,712,733 | 1/1973 | Giaimo, Jr. | 118/637 X |
| 3,781,107 | 12/1973 | Ruhland | 15/256.3 X |
| 4,593,407 | 6/1986 | Konishi et al. | 382/46 |
| 4,692,017 | 9/1987 | Maczuszenko et al. | 118/657 X |

FOREIGN PATENT DOCUMENTS 3406261 8/1985 Fed. Rep. of Germany.

OTHER PUBLICATIONS

Japanese Patent Abstract (11) 60-70485(A) vol. 9, No. 210 (P-383) [1933] Aug. 28, 1985. "Feeding Method of Trans...".
Japanese Patent Abstract (11) 60-229038(A) vol. 10 No. 93, (P-445) [2150] Apr. 10, 1986. "Copying Machine".
Japanese Patent Abstract (11) 59-79274(A) vol. 8 No. 192 (P-298) [1629] Sep. 4, 1984 "Electrostatic Recording Dev.".
Japanese Patent Abstract (11) 61-144666(A), vol. 10 No. 341 (P-517) [2397] Nov. 18, 1986 "Image Forming Device...".
Xerox Disclosure Journal, "Magnetic Guard Against Debris in Paper Tray", vol. 1, No. 6, Jun. 1976 Carl M. Cavitt.
Xerox Disclosure Bulletin "Magnetic Devices for Capturing Foreign Metallic Objects", vol. 10 No. 6, 11&12 1985 I. F. Palumbo.

Primary Examiner—Leo P. Picard
Assistant Examiner—Christopher Horgan
Attorney, Agent, or Firm—Hill, Steadman & Simpson

[57] ABSTRACT

A high-speed printing device is provided with a particle trap (30), arranged in the paper channel in the paper transport direction upstream of the printing area (15, 49), for intercepting particles, i.e. paper clips, entrained with he recording carrier (12). The particle trap has a passage slot (95), which is dimensioned to correspond to the size of the particles to be intercepted, for the recording carrier (12).

8 Claims, 4 Drawing Sheets

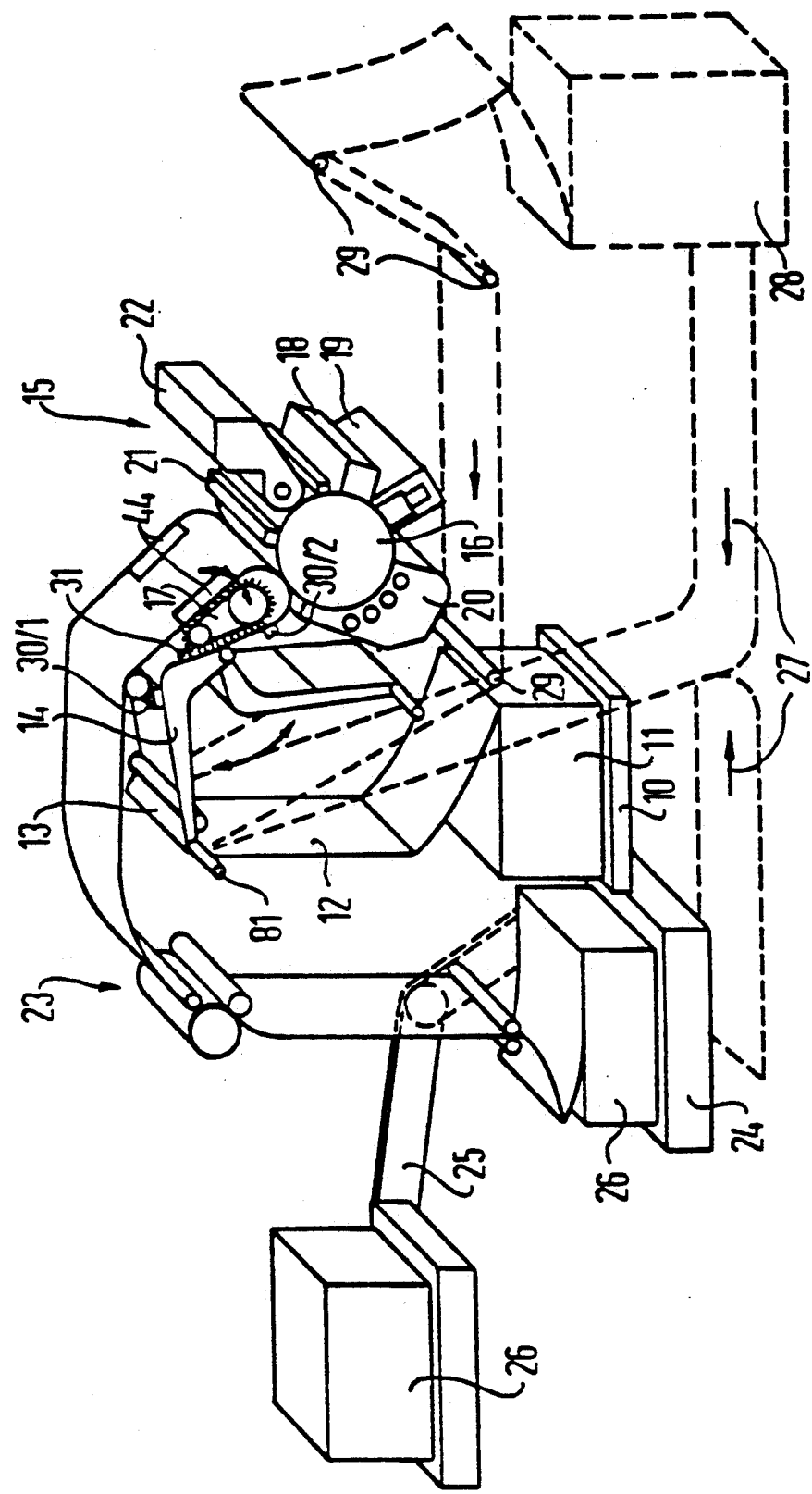

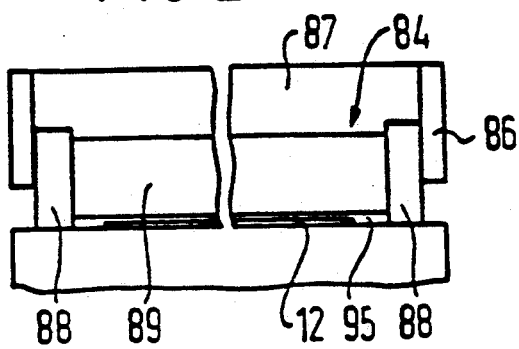
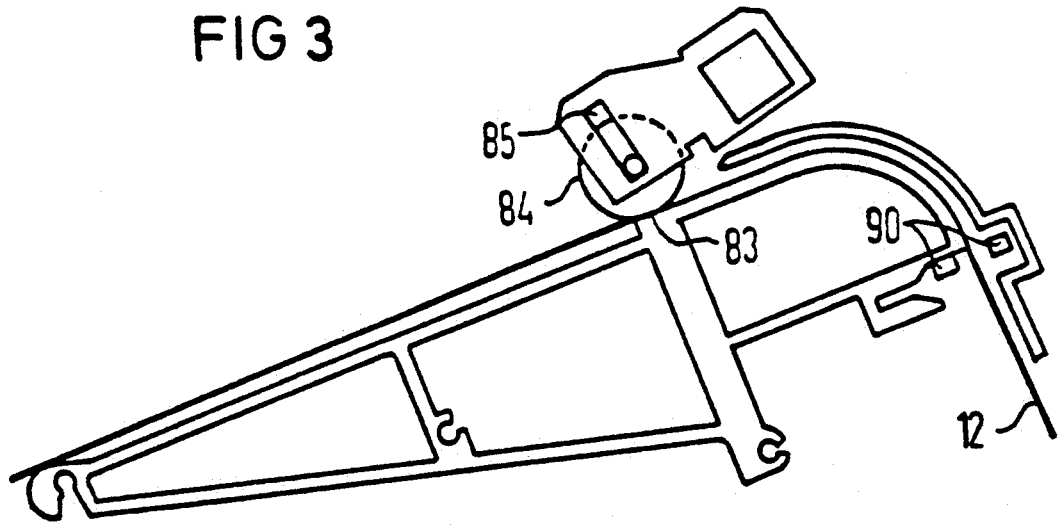

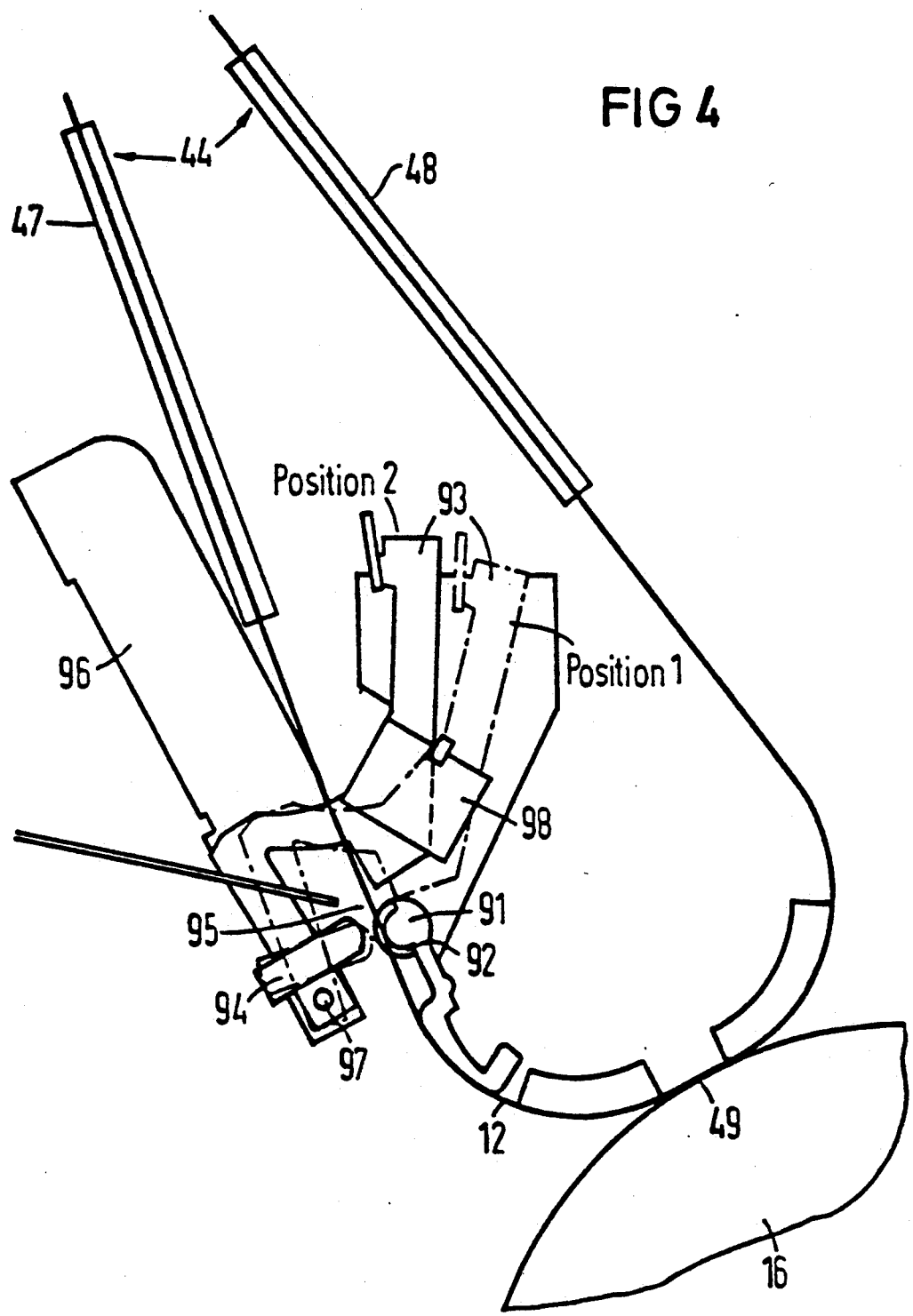

HIGH-SPEED PRINTING DEVICE HAVING A PARTICLE TRAP ARRANGED IN THE PAPER CHANNEL

BACKGROUND OF THE INVENTION

1. Field of the Invention

The invention relates to a high-speed printing device in which a recording carrier is fed to a printing station via a paper channel.

2. Description of the Related Art

Non-mechanical printers, such as for example laser printers, printers operating with LED combs, magnetic printers or printers operating with ink pressure are generally used as modern high-speed printing devices. These are generally known and have been applied successfully.

In printers operating according to the principle of electrophotography, a latent image is produced on a photoconductive drum with the aid of a light source which is controlled in a character-dependent manner, this image being inked in a developer station by applying toner and then transferred onto a recording carrier in a subsequent transfer station. The image, which is located loosely on the recording carrier and consists of toner, is then fixed with the aid of a fixing device.

The photoconductive drums, used as intermediate carriers, of electrophotographic printers, whether they are made of inorganic or organic material, have a sensitive surface which can be easily scratched. Metal particles, e.g. paper clips, which may be entrained with the recording carrier, can damage the surface of the photoconductive drum, which leads to a fault on the printed image which can no longer be corrected.

With non-mechanical printing devices which operate with ink pressure, whether using a head which is moved line by line or an ink comb, it is also possible that, due to the close spacing required between ink outlet nozzles and recording carrier, a particle which is entrained with the recording carrier can lead to faults in the writing operation or to damage to the ink head or ink comb.

In order to prevent the ingress of particles, it is therefore customary in high-speed printing devices of every kind to cover or encapsulate the paper feed.

However, high-speed printing devices are generally operated in conjunction with EDP (electronic data processing) systems and operated by the same operating personnel. For this reason, the printing devices must be designed in such a way that virtually interruption-free printing is ensured. Thus, after a paper stack is consumed, it must be possible to insert a new stack very quickly without a substantial interruption time. For this reason, it is necessary to design the printing device in an ergonomically optimum fashion; this applies in particular to the insertion and removal of the paper and to the maintenance of the overall system. For this reason, it must be possible to open the printing device wide with the purpose of inserting the recording carrier. Thus, there is a risk of particles such as paper clips or the like getting into the region of the recording carrier during insertion and becoming stuck there, for example, due to electrostatic forces.

SUMMARY OF THE INVENTION

In order to be able to intercept these particles, it is known from the publications JP-A-60-229 038 (Abstract) and Xerox Discl. Journal, Vol. 1, No. 6, page 63 to arrange particle traps which intercept particles magnetically.

It is also known from the publication JP-A-71-144 666 to detect electrically particles which have penetrated into the paper channel with the aid of an electrode and, if required, to switch off the paper transport.

The object of the invention is to provide for printing devices of the type mentioned at the beginning a device which permits particles entrained by the recording carrier to be intercepted so that damage to the printing device does not occur. The device is to be of simple and economical design and, in particular, is not to impede the guidance of paper.

This object is achieved in a high-speed printing device of the type mentioned at the beginning having a particle trap for intercepting particles entrained with the recording carrier arranged in the paper channel in the paper transport direction upstream of the printing area, the particle trap being configured as a mechanical particle trap with a passage slot, which is dimensioned to correspond to the size of the particles to be intercepted, for the recording carrier which has a paper saddle and a intercepting rod which is arranged at a distance from the paper saddle and spans the recording carrier.

Advantageous embodiments of the invention provide that the paper saddle and/or the intercepting rod are of swivel-away design. In a preferred embodiment, the passage slot has a structure which is wedge-shaped in cross-section so that entrained particles become jammed between the rod and the paper saddle.

The high-speed printing device may include, in the paper channel, a sensing device provided for the recording carrier, which sensing device interrupts the further recording carrier transport after determining that a recording carrier transport fault resulting from a particle intercepted in the particle trap has occurred. The sensing device is an opto-electronic sensing device.

The particle trap is preferably positioned on the transfer station of an electrophotographic printing device between paper tractors, arranged on the input side and output side upstream of the transfer area. Likewise, it is preferred that the intercepting rod be arranged on a swivellable lever which can be locked by means of locking elements.

Due to the fact that a particle trap for intercepting entrained particles is provided in the paper channel of the printing device in the paper transport direction upstream of the actual printing station, paper clips or other metal pieces entrained with the recording carrier cannot damage the printing station.

A passage slot dimensioned to correspond to the size of the particles to be intercepted permits the trouble-free passage of the recording carrier, but entrained particles become jammed in the passage slot and lead to a tearing of the paper or to an interruption of the paper transport.

This interruption of the paper transport is detected with the aid of an opto-electronic sensing device and the paper transport means in the printer is interrupted and, for example, a warning device on the operating display is activated.

In an advantageous embodiment of the invention, the particle trap contains a rod in the form of a particle bar which is arranged opposite a deflection profile of the transfer station. Particles entrained by the recording carrier become jammed between the particle bar and the deflection profile.

In order to remove the particles, the deflection profile with the transfer station can be swivelled away from the particle bar by means of an actuation rocker and the passage slot can thus be opened.

This permits the printing device to be rapidly restarted in the event of printing interruptions.

BRIEF DESCRIPTION OF THE DRAWINGS

An embodiment of the invention is illustrated in the drawings and described below in greater detail by way of example.

FIG. 1 shows a diagrammatic illustration of an electrophotographic printing device, FIG. 2 shows a diagrammatic front view of a particle trap, FIG. 3 shows a diagrammatic side view of a particle trap in the entry area of the paper guidance channel, FIG. 4 shows a diagrammatic sectional view of a transfer station of an electrophotographic printing device with the particle trap arranged therein in different operating states.

DETAILED DESCRIPTION OF THE PREFERRED EMBODIMENTS

Figure 5:
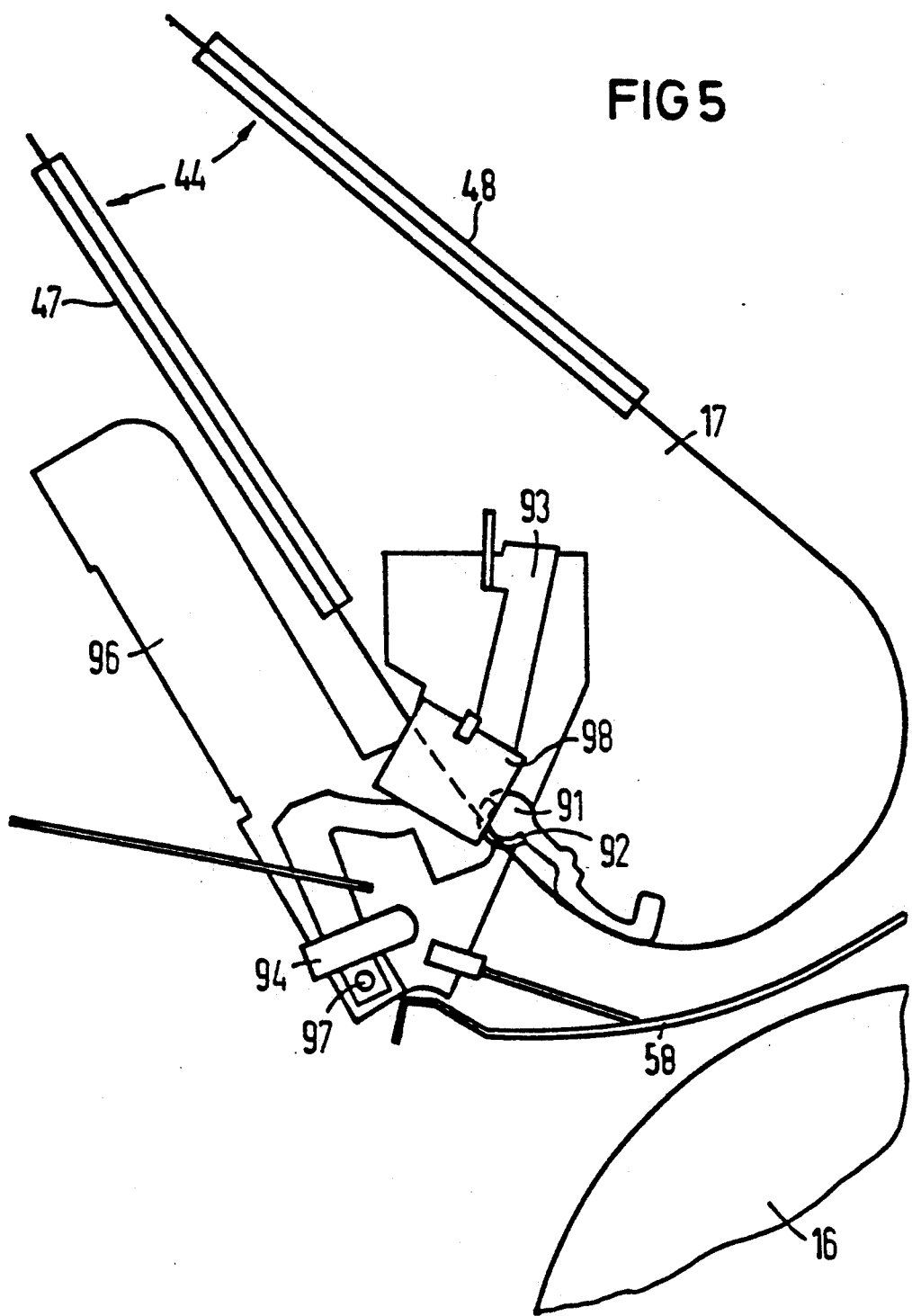
FIG. 5 shows a diagrammatic sectional view of the transfer station in accordance with FIG. 4 in the swivelled-away state with the opened particle trap.

A printing device operating according to the principle of electrophotography has a supply table 10 for receiving a supply stack 11 of prefolded continuous paper 12. The continuous paper is fed via a paper distributor device 13 and an actuation rocker 14 which is provided with paper guiding elements and can be swivelled away via an actuation handle 81 with a locking device, to the actual electrophotographic printing unit 15. This printing unit 15 has a transfer station 17, which can be swivelled to and away from a photoconductive drum 16, and devices arranged about the photoconductive drum 16 which are necessary for the electrophotographic process.

In order to generate a toner image on the continuous paper, the photoconductive drum 16, which is charged in the usual manner with the aid of a charging device 18, is discharged in a character-dependent manner by means of an LED character generator 19 and the charge image thus produced is inked in a developer station 20 with a developer mixture of toner particles and carrier particles. The toner image is then transferred onto the continuous paper 12 in the transfer station 17. After the transfer, the photoconductive drum 16 is discharged by means of a discharge station 21 and is cleaned in a cleaning station 22 and charged again by means of the charging device 18.

However, instead of the described electrophotographic process, it is also possible, for example, to use an electrostatic process or a magnetic process or even an ink comb which applies ink directly onto the continuous paper, in order to generate the toner image on the continuous paper 12.

The paper web 12 provided with a toner image is then fixed chemically or by means of heat in a fixing station 23 and deposited on a stacker table 24. In the illustrated exemplary embodiment of the printing device, the stacker table 24 is designed to swivel out by means of a swivel lever 25 in order to facilitate the removal of the printed paper stack 26.

If the printing device is coupled, for example, to a further printing device in order, for example, to permit printing on the front or rear side, the paper web 12 can also be fed directly to the paper distributor device 13 via external paper feed channels 29. It is also possible to use an external continuous the supply stack 28 as supply stack. In order to feed the paper web, separate paper feed elements with paper rollers 29 may be necessary in this case.

In order to prevent the ingress into the printing unit 15 of particles such as paper clips or other metal parts which damage the photoconductive drum 16, a particle trap 30, 30/1, 30/2 can be arranged at the entry area to the transfer station 17 or shortly upstream of the transfer region. The printing device also has a paper insertion device, which can be activated by means of the actuation rocker 14, with the associated paper brake 31, and paper tractors 44 as paper transport elements which are arranged upstream and downstream of the transfer point.

The particle trap in accordance with the exemplary embodiment in FIGS. 2 and 3 contains a paper saddle 83, arranged on the actuation rocker 14 shortly upstream of the deflection area 69, and a round metal rod 84 which spans the paper saddle 83 in accordance with the width of the recording carrier 12 and is guided in slots 85 of a lateral bracket 86. The bracket is attached by means of a crossbar (cross profile) 87 to the housing of the printing device. The metal rod 84 in turn has two lateral round guide areas 88 with a large diameter and an intercepting area 89, extending transversely over the paper web, with a smaller diameter. As a result, a passage slot for the paper 12 is produced in the intercepting area 89 between the paper saddle 83 and the metal rod 84.

A metal element, for example a paper clip, which has penetrated the passage slot becomes wedged in the passage slot and leads to the paper web 12 tearing. This tearing of the paper web 12 is detected by means of appropriate detectors, for example in the form of a light barrier 90 arranged in the deflection area 69, and the paper transport is stopped. In order to remove the particle, the metal rod 84 can be moved upwards in the slots 85 of the lateral bracket 86. The bracket 86 with the slots 85 is arranged by means of the crossbar 87 at such an angle with respect to the paper web that the wedging effect upon the ingress of metal particles is supported. It is to be understood by this that wedging of the metal piece to be intercepted with subsequent tearing of the paper reliably occurs.

In a preferred exemplary embodiment of the particle trap in accordance with FIGS. 4 and 5, the particle trap is arranged on the transfer station 17 between the input-side and output-side paper tractors 44 in the paper transport direction upstream of the transfer point 49. Thus, during a movement of the paper 12 both in the forward and rearward direction, the paper 12 cannot become jammed in the passage slot 95 of the paper trap since the paper 12 is always tensioned between the paper tractors 44.

The paper trap itself contains a deflection profile 91 arranged in the paper path of the transfer station 17, which profile extends over the width of the transfer station 17 and upon which the continuous paper 12 slides with its rear side, to which toner has not been applied. Spacing plates 92 are attached to the profile at the lateral ends. This results in a structure for the deflection profile 91 which corresponds to the metal rod 84 including the guide areas 88 of the exemplary embodiment in FIG. 2.

The particle bar 94 in the form of a metal rod can be swivelled onto the deflection profile by means of a lever 93, the particle bar 94 in the swivelled-on state resting on the spacing plates 92 and thus forming between deflection profile 91 with continuous paper 12 guided thereon a passage slot 95 (calibration aperture) for intercepting the particles.

The geometry of the entry into the calibration aperture 95 is of funnel-shaped design. It is thus ensured that wedging of the metal piece to be intercepted occurs, followed by tearing of the paper.

The lever 93 is mounted on a bearing block 96 for the swivel bearing 41 of the actuation rocker 14, specifically in a swivellable manner about a center of rotation 97. Furthermore, it has a locking device 98 which permits the lever 93 to be locked in two positions. These locking positions are sensed by means of a microswitch 99.

With the aid of this locking device 98, the lever 93 can be locked in two positions, specifically in a first position (position 1) in which the particle bar 94 is swivelled onto the deflection profile 91 and thus the particle trap is closed, and into a second position (position 2) in which the particle bar 94 is swivelled away from the deflection profile 91. This swivelled-away position 2 is necessary if, removably arranged on the recording carrier labels which would otherwise become jammed in the passage slot 95, are to be printed on using the printing device. The different positions of the lever are detected by means of the microswitch 99 and reported to the device control. The device control thus monitors the position of the lever 93.

In both lever positions in FIG. 4 the transfer station 17 is in the operating position, that is to say in a position swivelled onto the photoconductive drum 16 with the actuation rocker 14 locked.

If a metal piece becomes wedged in the calibration aperture 95 in this operating position, the paper web tears and this tear is detected by the light barrier 19 and the paper transport is stopped. In order to remove the particles, the transfer station 17 is swivelled away by means of the actuation rocker 14 in accordance with FIG. 5. As a result, paper guiding elements 58 swivel into the paper transport channel and protect the photoconductive drum 16. Particles which drop out of the calibration aperture 95 when it opens therefore cannot damage the photoconductive drum 16.

The monitoring of the paper transport by means of the light barrier 90 can be carried out with the aid of the actual device control of the printing device, which is not illustrated here and which can be configured, for example, in accordance with U.S. Pat. No. 4,593,407. If the paper transport is interrupted and the light barrier 90 thus emits a corresponding interrupt signal to the device control, the device control stops the further drive of the paper transport elements 44 which are configured in the present embodiment of the invention as paper tractors. The interruption is indicated on a corresponding control display and the operator can remove the intercepted metal objects by simply swivelling away the actuation rocker 14 by means of a handle 81 and reinserting the continuous paper via the insertion channel which results from the swivelling away of the actuation rocker.

I claim:

1. A particle trap for a high-speed printing device in which a recording carrier is fed to a printing station via a paper channel, comprising: a particle trap means for intercepting particles entrained with the recording carrier, said particle trap means being arranged in the paper channel in a paper transport direction upstream of the printing station, the particle trap means comprising a mechanical particle trap defining a passage slot, which is dimensioned to correspond to sizes of particles to be intercepted, through which the recording carrier passes, said particle trap means comprising a paper saddle and an intercepting rod which is arranged at a distance from the paper saddle to define said passage slot and which spans the recording carrier.

2. A particle trap for a high-speed printing device according to claim 1, wherein the paper saddle is mounted to and/or the intercepting rod swivel-away from a position defining said passage slot.

3. A particle trap for a high-speed printing device according to claim 1, wherein said particle trap means includes a structure which is wedge-shaped in cross-section so that entrained particles become jammed between said intercepting rod and said paper saddle.

4. A particle trap for a high-speed printing device according to claim 1, further comprising: a sensing device provided for the recording carrier in the paper channel, said sensing device being connected to interrupt further recording carrier transport after determining a recording carrier transport fault resulting from a particle intercepted in the particle trap.

5. A particle trap for a high-speed printing device according to claim 4, wherein the sensing device is an opto-electronic sensing device.

6. A particle trap for a high-speed printing device according to claim 1, wherein the high speed printing device includes a transfer station with a transfer area for printing and paper tractors arranged both at an input side of the transfer area and an output side of the transfer area for moving paper in a printing direction through the transfer area, the particle trap being mounted on the transfer station and preceding the transfer area relative to the printing direction.

7. A particle trap for a high-speed printing device according to claim 1, further comprising: a swivellable lever on which is mounted said intercepting rod, and locking elements mounted to lock said swivellable lever in position.

8. A particle trap for a high-speed printing device according to claim 1, wherein the intercepting rod is mounted to swivel-away from a position defining said passage slot.

* * * * *